Dec. 19, 1972 R. L. BYRUM Plant Pat. 3,272
ROSE PLANT
Filed April 29, 1971
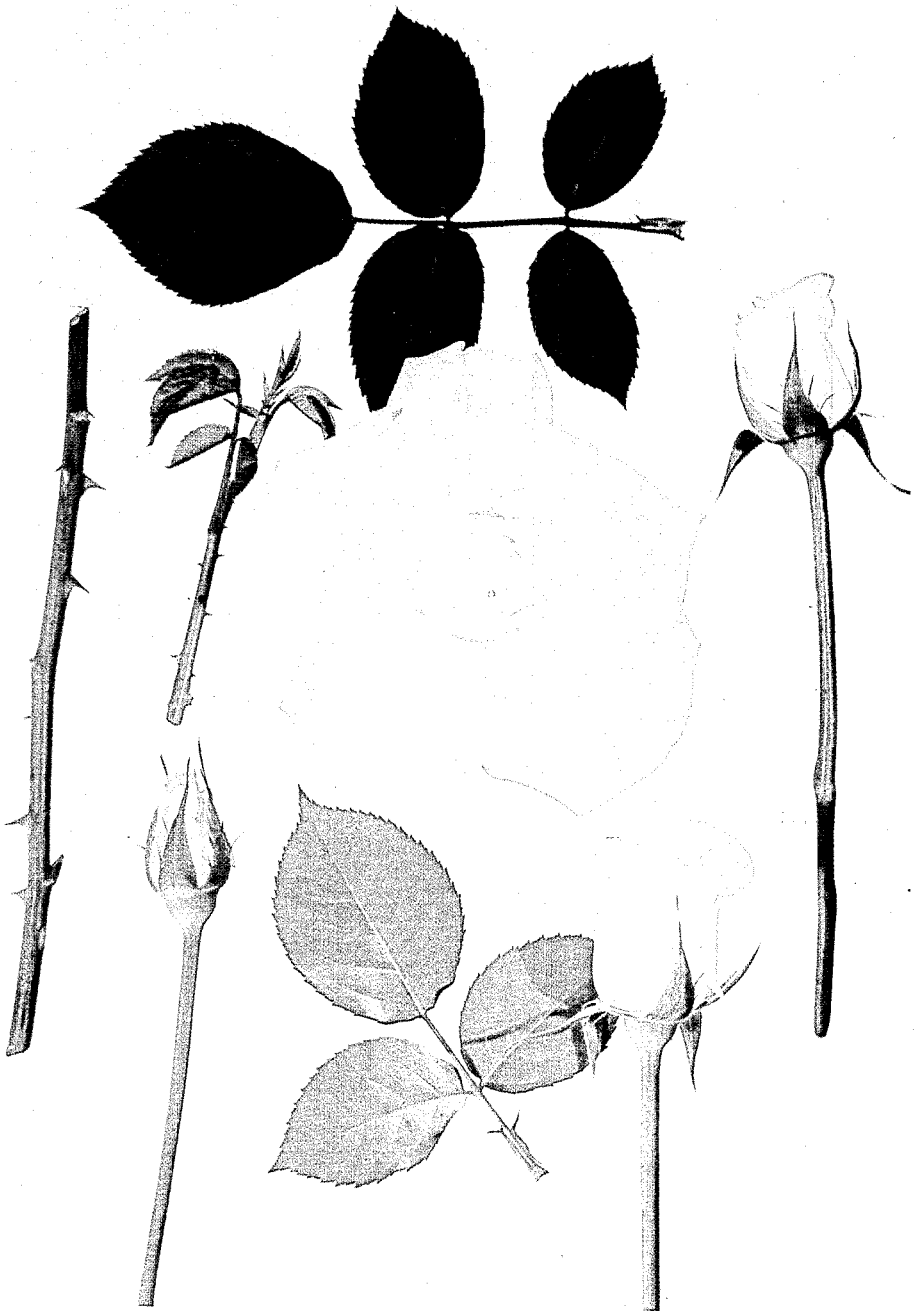
INVENTOR.
ROY L. BYRUM
BY Rummler & Snow
Attys.

United States Patent Office

Plant Pat. 3,272
Patented Dec. 19, 1972

3,272

ROSE PLANT

Roy L. Byrum, Richmond, Ind., assignor to Joseph H. Hill Company, Richmond, Ind.

Filed Apr. 29, 1971, Ser. No. 138,724
Int. Cl. A01h 5/00
U.S. Cl. Plt.—15 1 Claim

ABSTRACT OF THE DISCLOSURE

A new variety of hybrid tea rose developed as a seedling for greenhouse production of cut flowers and distinguished by the better color of its blooms over that of its parents, by the relative ease of its propagation, by its very strong resistance to disease and mildew, and by the fact that it is extremely fragrant for a hybrid rose and in comparison with most modern varieties.

BACKGROUND OF THE INVENTION

This new variety of yellow rose plant has resulted from breeding efforts carried on by me at Richmond, Indiana, with the object of developing a greenhouse cut flower production plant that would be easier to propagate and originated as a seedling of Golden Wave (P.P. 2105) × Anniversary (P.P. 2084) as the pollen parent. This cross was made in the hope of capturing the good qualities of both parents and at the same time finding a plant that could be more readily propagated on a commercial scale. This seedling came from a crossing made in March 1965 and the first flower was produced in October 1966. The new plant and its blooms appeared to have the desired growth and color characteristics and was therefore selected for propagation and trial. Subsequent asexual propagation of this new plant was carried on by me and under my supervision at Richmond, Ind., through successive generations and by the experience has demonstrated that the desired objective of easier propagation has been achieved.

This new variety of rose plant has also been propagated by budding at Hamilton City, Calif., and successive propagation in California and Indiana has shown that its distinguishing characteristics, including its improved coloring and growth, are firmly fixed and hold true from generation to generation.

DESCRIPTION OF THE DRAWING

My new variety of rose plant is illustrated by the accompanying drawing which is a photographic representation, in full color and as closely accurate as is reasonably possible by means of conventional color reproduction materials and procedures, showing typical specimens of the bud in various stages of opening, from the time the sepals first divide, a face view of a fully opened flower, upper and underside views of mature leaves, a typical specimen of new wood with young leaves, and a typical piece of the mature wood.

DESCRIPTION OF THE NEW PLANT

The following is a detailed description of my new variety of rose plant with color designations according to Royal Horticultural Society Horticultural Colour Chart, by Robert S. Wilson, and Koster's "Color Guide," identified herein as (W) and (K), respectively.

*The plant*

Origin: Seedling.
Parentage:
*Seed Parent.*—Golden Wave, Plant Patent 2105;
*Pollen parent.*—Anniversary, Plant Patent 2084.
Classification: Hybrid tea.

Type: Greenhouse grown for cut flowers.
Form: Bush.
Growth: Free and vigorous.
Habit: Upright and much branched, with canes of medium diameter.
Main stems: Color—Spinach Green 0960/1 (W).
*Thorns.*—Several, of medium length and hooked downwardly from a short narrow base.
*Color.*—Van Dyck Brown, Plate No. 96 (K).
*Prickles.*—None. *Hairs*: None.
Branches: Color—Spinach Green 0960/2 (W).
*Thorns.*—Several, medium length, hooked downwardly, with base short and narrow.
*Color.*—Erythrite Red 0027/1 (W) at base gradually changing to 0027/2 (W) toward tip.
*Prickles.*—None. *Hairs*: None.
New shoots: Color—Pansy Purple 928/2 (W).
*Thorns.*—Medium length, hooked downwardly with short and narrow base.
*Color.*—Pansy Purple 928/2 (W).
*Prickles.*—None. *Hairs*: None.
Foliage:
*Leaves.*—Shape—odd pinnate. Size—large, heavy and leathery.
*Leaflets.*—Shape—ovate, with acuminate apex, round base and simply serrate margin.
*Color.*—Mature, upper surface—Spanich Green 0960 (W) (nearest color); Mature, under surface—Apple Green Plate #77 (K), (nearest color); Young, upper surface—Purple Madder 1028/3 (W); Young, under surface—Pansy Purple 928/3 (W).
*Rachis.*—Medium heavy. Upper side: Smooth and grooved. Under side: Sparsely prickly.
*Stipules.*—Medium length, medium width, with short points turning outwardly at an angle of less than 45°.

*The bud*

Form:
*Before calyx breaks.*—Short pointed ovoid with a conspicuous neck and with foliaceous appendages on the bud surface having parts extending beyond bud tip a distance of about ¼ or more of the bud length.
*As first petal opens.*—Long pointed.
Size: Medium large—As calyx breaks and first petals open.
Color:
*Calyx.*—Lettuce Green 861/3 (W) overlaid with shades of Mahogany, Plate #95 (K).
*Bud.*—As calyx breaks—Lemon Yellow 4/1 (W).
*Petals.*—As first petals open: Outside—Aureolin 3/1 (W) at base gradually changing to 3/2 at top; Inside—Aureolin 3 (W) at base changing through 3/1 to 3/2 (W) at top.
Character of opening: The bud opens well in greenhouse.
Peduncle: Strong and erect, of medium length and diameter.
*Bark.*—Entirely smooth.
*Color.*—Scheeles Green 860/1 (W).
*Thorns.*—None. *Prickles*: None. *Hairs*: None.
Sepals: Permanent, spear shaped and of medium length. Color: Inside of sepals—Scheeles Green 860/3 (W) overlaid with white fuzz; outside of sepals—Scheeles Green 860/3 (W).

*The flower*

Blooming habit: Continuous and abundant in greenhouse. Outdoor blooming has not been observed.
Size: Medium large—3½ to 4½ inches in diameter.
Form: Full and high centered at first becoming open and high centered at maturity.

Borne: Singly on strong stems of medium length.

Petalage: Semi-double with 25 to 30 petals.

*Arrangement.*—Regular. Petals remain tightly rolled outward at first opening and become loosely rolled outward at maturity.

*Shape.*—Obovate, with retuse apex having one notch.

*Texture.*—Moderately thick and leathery.

*Appearance.*—Shiny, both inside and outside.

*Color.*—The following describes a newly opened flower grown in greenhouse at Richmond, Ind., and blooming in August 1970: Outside, Intermediate and Inner Petals: Outside surface—Aureoline 3/1 (W) at base of petal, gradually changing to 3/2 (W) at top; Inside surface—Aureolin 3 (W) at base changing through 3/1 to 3/2 (W) at top of petal. The following describes a flower that was open for three days in greenhouse at Richmond, Ind., in October 1970:

*Outside petals.*—Outside and inside surfaces—Primrose Yellow 601/1 (W) at base, changing to 601/3 (W) at tip of petal.

*Intermediate and inside petals.*—Outside surface and inside surfaces: Primrose Yellow 601/1 (W) at base, changing to 601/2 (W) at tip.

General color effect of open bloom:

*Newly opened flower.*—Empire Green 603/1 (W);

*Three days opened flower.*—Primrose Yellow 601/3 (W).

Fragrance: Penetrating tea (in greenhouse).

Persistence: Petals persist in greenhouse.

Lasting quality: Cut flowers grown in greenhouse kept very well for 4 to 5 days at living room temperatures in October 1970.

*Reproductive organs*

Stamens: Many in number, arranged regularly about the pistils.

*Anthers.*—Medium, all open at once. Color: Indian Yellow 6/1 (W).

*Filaments.*—Of medium length, most have anthers. Color: Buttercup Yellow 5/2 (W).

*Pollen.*—Abundant. Color: Orange Buff 507/2 (W).

Pistils: Many in number.

*Styles.*—Even, of medium length, thin and bunched. Color: Cardinal Red 822 (W).

*Stigma.*—Color: Amber Yellow 505/3 (W).

Ovularies: Some protruding from calyx.

This new variety of rose plant not only retains the good qualities of its parents but also exhibits a better color and better foliage than its seed parent, a stronger, more uniform color than its pollen parent, and is much easier to propagate than either of its parents. The new plant is very resistant to diseases and mildew, as compared with other varieties grown under similar conditions at Richmond, Ind., and at Hamilton City, Calif., and is extremely fragrant in comparison with most modern roses.

I claim:

1. A new and distinct variety of rose plant substantially as herein shown and described, characterized by the more uniform and brighter yellow coloring of its blooms, its penetrating tea fragrance, its strong resistance to rose plant diseases and mildew, and the relative ease of its propagation for commercial exploitation.

No references cited.

ROBERT E. BAGWILL, Primary Examiner